United States Patent [19]

Darsow

[11] Patent Number: 5,861,521

[45] Date of Patent: Jan. 19, 1999

[54] PROCESS FOR THE HYDROGENATION OF ESTERS OF UNSATURATED FATTY ACIDS

[75] Inventor: Gerhard Darsow, Krefeld, United Kingdom

[73] Assignee: Bayer Aktiengesellschaft, Leverkusen, Germany

[21] Appl. No.: 546,344

[22] Filed: Oct. 20, 1995

[30] Foreign Application Priority Data

Oct. 28, 1994 [DE] Germany .......................... 44 38 547 .1

[51] Int. Cl.$^6$ ................................................. C07C 67/283
[52] U.S. Cl. .......................... 554/141; 554/145; 554/146; 502/102; 502/103; 502/258; 502/527
[58] Field of Search ............................ 554/141; 587/148, 587/146; 502/102, 103, 258, 527

[56] References Cited

U.S. PATENT DOCUMENTS 4,826,799  5/1989  Cheng et al. ............................ 502/301
5,407,886  4/1995  Schneider et al. ....................... 502/244

Primary Examiner—Gary Geist
Assistant Examiner—Deborah D. Carr
Attorney, Agent, or Firm—Sprung Kramer Schaffer & Briscoe

[57] ABSTRACT

Esters of unsaturated fatty acids or mixtures thereof can be hydrogenated by a catalysed liquid-phase hydrogenation with hydrogen to give saturated or partially saturated esters of fatty acids or ester mixtures of fatty acids by carrying out the hydrogenation continuously at a pressure of 50 to 350 bar and a reaction temperature of 40 to 150° C. on oxygen-free and support-free shaped bodies which are arranged in a fixed bed and made of pressed powders of elements of the iron subgroup of subgroup VIII of the Periodic Table of the Elements or their alloys with each other or their alloys with elements of subgroup VI; in addition, hydrogenation-inert elements can be present. The shaped bodies have a compressive strength of 20 to 250N on the curved shaped body surface and have an internal surface area of 10 to 90 m$^2$/g.

14 Claims, No Drawings

PROCESS FOR THE HYDROGENATION OF ESTERS OF UNSATURATED FATTY ACIDS

BACKGROUND OF THE INVENTION

1. Field of the Invention

The present invention relates to a novel, inexpensive, continuous process for the hydrogenation of esters of unsaturated fatty acids or ester mixtures of unsaturated fatty acids to give esters or ester mixtures of saturated or partially saturated fatty acids in which no undesirable higher monoalcohols or aldehydes which are characterized by an unpleasant odour or flavour are formed as by-products.

The hydrogenation of esters of unsaturated fatty acids or ester mixtures of unsaturated fatty acids allows compounds or compound mixtures having a higher or lower melting point to be prepared from the usually liquid unsaturated compounds.

From liquid vegetable or animal mixtures of glycerides of fatty acids, high-grade solid food fats can be produced in this manner which are extensively used as margarine or frying fats, but can also be used industrially (e.g. as lubricants).

2. Description of the Related Art

It is known to hydrogenate ester mixtures of unsaturated fatty acids discontinuously with hydrogen over Ni powder to give esters of saturated fatty acids (DRP 141 029).

It is further known to hydrogenate ester mixtures of unsaturated fatty acids discontinuously with hydrogen over mixed catalysts of the hydroxides, oxides or carbonates of Ni, Co, Fe with Cu or Pd, Pt or Ag to give esters of saturated fatty acids (U.S. Pat. No. 1,268,692).

It is further known to hydrogenate ester mixtures of unsaturated fatty acids semi-continuously with hydrogen in a plurality of series-connected discontinuous apparatuses using Ni powders or Ni on pulverulent kieselguhr as a support (GB 804 604, U.S. Pat. No. 2,932,658).

Moreover, it is known to hydrogenate ester mixtures of unsaturated fatty acids continuously with hydrogen on stationary Ni spirals located in a vertical column (GB 162 370, GB 203 218).

The course of the reaction can be illustrated, e.g. for the hydrogenation of methyl linoleate to give methyl stearate by the following reaction diagram:

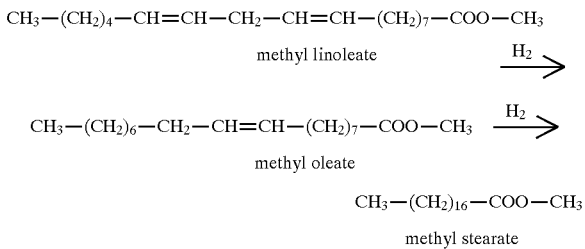

In the known processes for the hydrogenation of esters of unsaturated fatty acids or ester mixtures of unsaturated fatty acids, dicontinuous suspension processes (batch processes) are almost exclusively used in which the esters of fatty acids or ester mixtures of fatty acids are hydrogenated with hydrogen over pulverulent, predominantly Ni-containing, catalysts.

Discontinuous processes have the disadvantage that their capacity is very small relative to the reaction volume and there is thus a requirement for large reaction apparatuses and storage tanks. Energy consumption and labour requirements are relatively high.

Continuous powder catalyst processes which employ a plurality of hydrogenation reactors connected in cascade avoid some of these disadvantages. However, there remains the requirement of specifically repeatedly dosing the pulverulent catalysts, circulating them by pumping and quantitatively filtering them off from the reaction product. The catalyst slurry pumps are subject to high mechanical wear. The quantitative removal of the pulverulent catalysts from the reaction product is complex. In addition, there is a great danger of relatively rapidly decreasing the catalyst activity by the additional operations. It is therefore advantageous to allow the reaction to proceed over fixed catalysts. Such catalysts must have a high activity which must not decrease over a relatively long period, because frequent changes of catalyst in fixed-bed reactions are likewise complex.

The hydrogenation of ester mixtures of unsaturated fatty acids on stationary Ni spirals (see above) situated in a vertical column has previously been described as a continuous process. However, such a process operates with low efficiency and has not proved itself in practice because the metallic Ni spirals have only a relatively low active surface area (<1 m$^3$/g).

SUMMARY OF THE INVENTION

Surprisingly, it has now been found that esters of unsaturated fatty acids or ester mixtures of unsaturated fatty acids can be very readily hydrogenated continuously over support-free shaped bodies arranged in a fixed bed and made of oxygen-free metal powders or small particles, e.g. granulates of one or more elements of the iron subgroup of subgroup VIII of the Periodic Table (Mendeleev) to give esters or ester mixtures of saturated or partially saturated fatty acids. For this it can be useful to alloy the metals of the iron subgroup with activating elements of subgroup VI of the Periodic Table of the elements. The powders or small particles used in this can additionally contain small amounts of catalytically inactive elements (e.g. silicon, aluminium, titanium, carbon) without the high activity being diminished. The solid bodies must have a compressive strength of 20–250N and an internal surface area of 10–90 m$^2$/g.

The invention thus relates to a process for the continuous preparation of esters of partially or completely saturated fatty acids or mixtures of a plurality thereof by catalytic hydrogenation of esters of unsaturated fatty acids or mixtures of a plurality thereof, where the acid moiety of the esters contains 6–30 C atoms and the alcohol moiety is monohydric to trihydric and contains 1–20 C atoms, which is characterized in that the hydrogenation is carried out in the liquid phase at an H$_2$ pressure of 50–350 bar, at a 20–60-times molar amount of H$_2$, based on the stoichiometric amount and at a temperature of 40°–150° C. on oxygen-free and support-free catalysts arranged in a fixed bed which are present as pressed shaped bodies produced from metal powders or particles which have a compressive strength of 20–250N and an internal surface area of 10–90 m$^2$/g and in which the metal powders contain 65–100% by weight of one or more ferrous metals, 0–15% by weight of one or more metals of subgroup VI and 0–20% by weight of one or more hydrogenation-inert elements selected from the group consisting of aluminium, silicon, titanium and carbon, all based on the total weight of the metal powder or particles.

DETAILED DESCRIPTION OF THE INVENTION

The compressive strength of the support-free shaped bodies can be Determined in accordance with DIN 50 106.

Testing support-free shaped bodies for the internal surface areas in accordance with the claims and thus for usability for the process according to the invention can be carried out by methods which have been described by F. M. Nelsen and F. T. Eggertsen, Analyt. Chem. 30 (1958), pp. 1387–1390 and S. J. Gregg and K. S. W. Sing, Adsorption, Surface Area and Porosity, London 1982, chapters 2 and 6.

The iron subgroup of subgroup VIII of the Periodic Table of the Elements (Mendeleev) contains the elements iron, cobalt and nickel. The support-free shaped bodies to be used according to the invention contain one or more of these metals in amounts of at least 65, preferably at least 70, in particular at least 80, % by weight, based on the total weight of the support-free shaped bodies.

Subgroup VI of the Periodic Table of the Elements contains the elements chromium, molybdenum and tungsten. The support-free shaped bodies to be used according to the invention contain one or more of these metals in amounts of 0–15% by weight. When these metals are present, the metal powders contain at least 0.1, preferably 0.3, in particular at least 0.5, % by weight, based on support-free shaped bodies; they contain one or more of these metals in amounts of at most 15, preferably at most 10 and in particular at most 5, % by weight, based on support-free shaped bodies.

The support-free shaped bodies to be used according to the invention can, furthermore, contain—in each case based on support-free shaped bodies—up to 20, preferably up to 15, % by weight of other elements; examples of such elements which are not catalytically active comprise aluminium, silicon, titanium and carbon. According to a preferred embodiment, the support-free shaped bodies, apart from the metals of subgroups VIII and VI, contain no more than 10% by weight of aluminium and no more than 5% by weight of other elements.

For the hydrogenation process, pure hydrogen is used precompressed to a pressure of 50–350 bar, preferably 100 to 300 bar, with a 20 to 60-fold, preferably 20 to 40-fold, molar amount of hydrogen being employed, based on the stoichiometric amount.

The hydrogenation is performed continuously in the fixed-bed process on the support-free shaped bodies of the type described serving as hydrogenation catalysts in that the esters or ester mixtures of unsaturated fatty acids to be hydrogenated are allowed to flow either co-currently with the previously admixed hydrogen ascending from bottom to top over the shaped bodies packed into the hydrogenation reactor or else coming from the bottom in the opposite direction (counter-current process) to the hydrogen flowing in from the top.

Pure esters of unsaturated fatty acids or natural vegetable or animal ester mixtures of fatty acids are used.

The hydrogenation process is carried out at temperatures of 40° to 150° C. Lower temperatures require higher residence times or require a quantitative conversion to be dispensed with. Higher temperatures lead to the formation of undesirable fatty acid alcohols.

The hourly catalyst loading can be 200 to 1 000 g of ester or ester mixture of fatty acid/l of catalyst.

The hydrogenation reactor can either be a single high-pressure tube made of steel or a steel alloy which is wholly or partly filled with the support-free shaped bodies, in which case application on hurdles (wire baskets or the like) can be useful or else a jacketed high-pressure tube bundle whose individual tubes are wholly or partially filled with shaped bodies.

The production of the support-free shaped bodies can be performed by customary methods by pressing the metal powders or particles on tableting and pelleting machines under high pressure, where to improve the adhesive strength of the metal particles, graphite can also be used in amounts of 0.5–1.5% by weight, based on the total weight of the constituents forming the catalyst, or adhesives can be used in small amounts. The production of the support-free shaped bodies is preferably carried out in an oxygen-free atmosphere in order to avoid surface oxidations. The most effective and expedient for carrying out the reaction are tableted and pelleted shaped bodies having diameters of 3 to 7 mm. The compressive strength of the shaped bodies is of considerable importance and according to the invention has values of 20 to 250N, preferably 100 to 220N on the curved shaped body surface. Lower compressive strengths lead to shaped body disintegration or erosive wear which would cause metallic contamination of the reaction product. Higher values require a disproportionate effort in pressing without further advantages being achieved. The internal surface area of the shaped bodies is further of considerable importance which according to the invention has values of 10 to 90 m$^2$/g and is decisive for a conversion rate as quantitative as possible of the starting materials.

Under the reaction conditions described, in this manner, highly unexpectedly, high catalyst lives of 15 000 hours and more may be achieved, which leads to catalyst consumptions <0.1% by weight, based on the reaction product prepared.

The reaction mixture leaving the hydrogenation reactor is depressurized, the excess hydrogen being able to be collected and after compression has been carried out and supplementation of consumed hydrogen, being able to be reused. In the case of complete hydrogenation, the reaction mixture comprises more than 99% by weight of esters or ester mixtures of saturated fatty acids.

If only partial hydrogenation of the double bonds present is contemplated, the partially hydrogenated esters or ester mixtures of fatty acids, depending on the reaction temperature, can be produced according to a preset contemplated solidification point.

The oxygen-free and support-free fixed-bed catalysts to be used according to the invention, in contrast to support-containing catalysts, do not have a tendency to "bleed" i.e. do not have a tendency to transfer catalyst constituents in ionic or colloidal form into the solution phase of the substrate so that the substrate does not become contaminated by heavy metals which can usually likewise only be removed from the substrate with difficulty, for example using ion exchangers. The catalyst metals to be used can, for example after relatively long use of the catalyst, be readily worked up and reused, since the heavy metals do not have to be laboriously separated from a support material. In the case of polyfunctional compounds, for example in the case of only partially esterified polyhydric alcohols, there was furthermore a fear of the trend to form complex chelate compounds of the fatty soaps with the heavy metal ions which can only be removed with difficulty from the esters or ester mixtures; this fear does not arise with the catalysts to be used according to the invention.

The wholly or partially hydrogenated esters or ester mixtures of fatty acids produced have a content of catalyst constituents <1 ppm and can therefore be used in the food sector without further purification.

EXAMPLES

Example 1

A vertically upright, heat-insulated high-pressure tube made of stainless steel of 45 mm internal diameter and 1 m length was packed with 1.4 l of a hydrogenation catalyst produced by tableting Ni powder which, at a cylinder height of 5 mm and a diameter of 5 mm had a compressive strength of 147N on the cylinder periphery surface and an internal surface area of 33 m²/g. Per hour, 320 g of pure methyl linoleate (>99% by weight) were pumped ascending from bottom to top through this tube together with the 20-times molar amount of highly pure hydrogen under a pressure of 300 bar.

Methyl linoleate and hydrogen were first run together through a heat exchanger and heated so that they entered the high-pressure tube at a temperature of 120° C. The mixture of liquid reaction product and excess hydrogen leaving the high-pressure tube was run into a separator, from where the hydrogen, after replacement of the amount consumed, was pumped back, together with new methyl linoleate, into the preheater and from there back into the high-pressure tube.

The colourless, clear and odourless melt of the reaction product, after cooling to a temperature <60° C. and pressure reduction to atmospheric pressure was studied by gas chromatography. It no longer contained unsaturated portions (iodine value: <0.1).

The content of methyl stearate was >99% by weight, and the solidification point was 37°/38° C.

The catalyst was unchanged in activity after a running time of 4 800 hours, so that the composition of the reaction product did not change over this period.

Example 2

In a high-pressure tube as in Example 1, at a temperature of 120° C. and a hydrogen pressure of 300 bar, per hour, an amount of 280 g of soya oil (iodine value: 121, acid number: <0.1) was hydrogenated. The catalyst had been produced by tableting a powdered Ni/Al/Si alloy having an Al content of 5.4% by weight and an Si content of 0.2% by weight.

The tablets, at a cylinder height of 3 mm and a diameter of 3 mm, had a compressive strength of 148N on the cylinder peripheral surface and an internal surface area of 61 m²/g.

After a running time of 3 300 hours, the conversion rate of the soya oil used was >99.0% by weight. The reaction product obtained was colourless and odourless and had a solidification point of 61° C. and an iodine value <1 and an acid number <0.1. The Ni/Al/Si content was <1 ppm.

Example 3

In a high-pressure tube as in Example 1, at a temperature of 55° C. and a hydrogen pressure of 300 bar, per hour, an amount of 750 g of soya oil (iodine value: 121, acid number: <0.1) was hydrogenated. The catalyst had been produced by tableting a powdered Ni/Al alloy having an Al content of 4.1% by weight.

The tablets, at a cylinder height of 3 mm and a diameter of 3 mm, had a compressive strength of 142N on the cylinder peripheral surface and an internal surface area of 68 m²/g. The reaction product obtained was colourless and odourless and had a solidification point of 36° C. and an iodine value of 22 and an acid number <0.1. The Ni/Al content in the reaction product was <0.1 ppm.

The catalyst was unchanged in activity after a running time of 5 400 hours, so that the composition of the reaction product did not change over this period.

Example 4

In a high-pressure tube as in Example 1, at a temperature of 85° C. and a hydrogen pressure of 200 bar, the hydrogen, in reverse reaction flow, was run in the opposite direction to sunflower seed oil ascending as in Example 1 (iodine value: 128, acid number: <0.19), an amount equal to that in Example 1 being hydrogenated per hour. The catalyst had been produced by tableting a powdered Ni/Fe alloy. The alloy contained an iron proportion in the nickel of 15% by weight. The tablets, at a cylinder height of 5 mm and a diameter of 5 mm, had a compressive strength of 137N on the cylinder peripheral surface and an internal surface area of 74 m²/g.

The colourless, clear and odourless melt of the reaction product was isolated after cooling to a temperature <60° C. and reducing pressure to atmospheric pressure and had a solidification point of 56° C. and an iodine value of 2 and an acid number <0.1. The Ni/Fe content of the melt was <0.1 ppm.

The catalyst was unchanged in activity after a running time of 1 200 hours, so that the composition of the reaction product did not change over this period.

Example 5

In a high-pressure tube as in Example 1, at a temperature of 48° C. and a hydrogen pressure of 300 bar, per hour, an amount of 750 g of sunflower seed oil (iodine value: 128, acid number: <0.1) was hydrogenated. The catalyst had been produced by tableting a powdered Ni/Fe alloy. The alloy contained an Fe proportion in Ni of 15% by weight. The tablets, at a cylinder height of 5 mm and a diameter of 5 mm, had a compressive strength of 137N on the cylinder peripheral surface and an internal surface area of 74 m²/g.

The colourless, clear and odourless melt of the reaction product was isolated after cooling to a temperature <40° C. and decompressing to atmospheric pressure and had a solidification point of 32° C. and an iodine value of 26 and an acid number <0.1. The Ni/Fe content of the melt was <0.1 ppm.

The catalyst was unchanged in activity after a running time of 2 600 hours.

Example 6

A vertically upright, heat-insulated high-pressure tube made of stainless steel of 45 mm internal diameter and 1 m length was packed with 1.4 l of a hydrogenation catalyst produced by tableting powder of an Ni/Mo alloy having an Mo content of 1.75%, which catalyst had, at a cylinder height of 5 mm and a diameter of 5 mm, a compressive strength of 191N on the cylinder peripheral surface and an internal surface area of 58 m²/g. Through this tube was pumped ascending from bottom to top 400 g of rapeseed oil (iodine value: 102.5, acid number: <1) per hour together with the 30-times molar amount of highly pure hydrogen under a pressure of 300 bar.

Rapeseed oil and hydrogen were brought to a temperature of 90° C. before entry into the high-pressure tube.

The colourless, clear and odourless melt of the reaction product was isolated after cooling to a temperature <60° C. and decompressing to atmospheric pressure and had a solidification point of 55° C. and an iodine value of 17.6 and an acid number <1. The Ni/Mo content of the melt was <0.1 ppm.

The catalyst was unchanged in activity after a running time of 2 800 hours, so that the composition of the reaction product did not change over this period.

Example 7

In a high-pressure tube as in Example 1, at a temperature of 110° C. and a hydrogen pressure of 300 bar, 360 g of a castor oil having characteristic odour (iodine value: 84, acid number: 4, hydroxyl number: 6) were hydrogenated per hour. The catalyst was produced by tableting powder of an Ni/Mo/Al alloy having an Mo content of 1.02% by weight and an Al content of 5.1% by weight. The tablets, at a cylinder height of 5 mm and a diameter of 5 mm, had a compressive strength of 210N on the cylinder peripheral surface and an internal surface area of 71 m²/g.

The reaction product obtained was colourless and odourless and at a solidification point of 76° C. had an iodine value of 7 and a hydroxyl number of 6. The Ni/Mo content was <0.1 ppm.

The catalyst was unchanged in activity after a running time of 2 400 hours.

Example 8

In a high-pressure tube as in Example 1, at a temperature of 55° C. and a hydrogen pressure of 300 bar, castor oil (iodine value: 84, acid number: 4, hydroxyl number: 6) was hydrogenated in an amount equal to that as in Example 1. The catalyst had been produced by tableting a powdered Ni/W alloy. The alloy had a W content of 1.4%. The tablets, at a cylinder height of 3 mm and a diameter of 3 mm, had a compressive strength of 162N on the cylinder peripheral surface and an internal surface area of 68 m²/g.

The reaction product obtained was colourless and odourless and at a solidification point of 38° C. had an iodine value of 18 and an acid number of 4.

The catalyst was unchanged in activity after a running time of 1 900 hours.

What is claimed is:

1. A process for the continuous preparation of esters of partially or completely saturated fatty acids or mixtures of a plurality thereof by catalytic hydrogenation of esters of unsaturated fatty acids or mixtures of a plurality thereof, where the acid moiety of the esters contains 6 to 30 C atoms and the alcohol moiety is monohydric to trihydric and contains 1 to 20 C atoms, wherein the hydrogenation is carried out in a hydrogenation reactor in the liquid phase at an $H_2$ pressure of 50 to 350 bar, at a 20 to 60-times molar amount of $H_2$, based on the stoichiometric amount and at a temperature of 40° to 150° C. on oxygen-free and support-free catalysts arranged in a fixed bed which are present as pressed shaped bodies produced from metal powders or particles which have a compressive strength of 20 to 250N on the curved shaped body surface and an internal surface area of 10 to 90 m²/g and in which the metal powders contain 65 to 100% by weight of one or more ferrous metals, 0 to 15% by weight of one or more metals of subgroup VI and 0 to 20% by weight of one or more hydrogenation-inert elements selected from the group consisting of aluminium, silicon, titanium and carbon, all based on the total weight of the metal powder or particles.

2. The process of claim 1, wherein the metal powders or particles contain 70 to 100% by weight of one or more iron subgroup metals.

3. The process of claim 2, wherein the metal powders or particles contain 80–100% by weight of one or more iron subgroup metals.

4. The process of claim 1, wherein the metal powders or particles, when metals of subgroup VI are present, contain these at 0.1 to 15% by weight.

5. The process of claim 4, wherein the metals of the subgroup VI are present at 0.3 to 10% by weight.

6. The process of claim 5, wherein the metals of the subgroup VI are present at 0.5 to 5% by weight.

7. The process of claim 1, wherein the metal powders or particles, when hydrogenation-inert elements are present, have a content of 0 to 10% by weight of aluminium and 0 to 5% by weight of each of the elements Si, Ti and C.

8. The process of claim 7, wherein the total content of the hydrogenation-inert elements is 0 to 15% by weight.

9. The process of claim 8, wherein the total content of the hydrogenation-inert elements is 0 to 10% by weight.

10. The process of claim 1, wherein the shaped bodies are cylindrical or spherical and have diameters of 3 to 7 mm.

11. The process of claim 1, wherein the shaped bodies are those having a compressive strength of 100 to 220N on the curved shaped body surface.

12. The process of claim 1, wherein the hydrogenation is carried out at an $H_2$ pressure of 100 to 300 bar.

13. The process of claim 1, wherein a 20 to 40-times molar $H_2$ amount is employed.

14. The process of claim 1, wherein the unsaturated fatty acid ester to be hydrogenated passes through the hydrogenation reactor ascending from bottom to top, while the hydrogen required for the hydrogenation is either pumped into the reactor together with the unsaturated ester or is conducted in the opposite direction to this flowing from top to bottom.

* * * * *